United States Patent
Heismann et al.

(10) Patent No.: US 11,069,439 B2
(45) Date of Patent: Jul. 20, 2021

(54) METHOD FOR CONTROLLING AN EVALUATION DEVICE FOR MEDICAL IMAGES OF PATIENT, EVALUATION DEVICE, COMPUTER PROGRAM AND ELECTRONICALLY READABLE STORAGE MEDIUM

(71) Applicant: Siemens Healthcare GmbH, Erlangen (DE)

(72) Inventors: Bjoern Heismann, Erlangen (DE); Razvan Ionasec, Nuremberg (DE)

(73) Assignee: SIEMENS HEALTHCARE GMBH, Erlangen (DE)

( * ) Notice: Subject to any disclaimer, the term of this patent is extended or adjusted under 35 U.S.C. 154(b) by 84 days.

(21) Appl. No.: 16/200,896

(22) Filed: Nov. 27, 2018

(65) Prior Publication Data

US 2019/0164643 A1    May 30, 2019

(30) Foreign Application Priority Data

Nov. 28, 2017  (EP) .................................... 17204143

(51) Int. Cl.
*G16H 30/40* (2018.01)
*G16H 30/20* (2018.01)
(Continued)

(52) U.S. Cl.
CPC .......... *G16H 30/40* (2018.01); *G06T 7/0016* (2013.01); *G06T 7/33* (2017.01); *G16H 30/20* (2018.01)

(58) Field of Classification Search
CPC ....... G06F 19/321; G06T 7/0016; G06T 7/33; G16H 30/20
See application file for complete search history.

(56) References Cited

U.S. PATENT DOCUMENTS

2007/0041660 A1    2/2007  Mahesh et al.
2009/0097778 A1*   4/2009  Washburn ................ G06T 7/33
                                            382/294

(Continued)

FOREIGN PATENT DOCUMENTS

EP         1755059 A1    2/2007
WO    WO 2010029470 A1   3/2010

OTHER PUBLICATIONS

European Search Report Application No. 17204143.6 dated Jun. 15, 2018.

*Primary Examiner* — Ross Varndell
(74) *Attorney, Agent, or Firm* — Harness, Dickey & Pierce, P.L.C.

(57) ABSTRACT

A method for controlling an evaluation system for medical images of a patient is proposed. Medical images of the patient acquired at different time points are stored in an image database. Upon reception of a user command associated with a time-dependent evaluation command including at least one evaluation parameter describing an evaluation to be performed and identification information describing the patient, medical images of the patient fulfilling a relevancy criterion depending on the evaluation parameter and acquired at different time points are retrieved from the image database. The retrieved images are registered to each other in at least one registration process. Finally, a composite evaluation image data set including a time series of evaluation images is derived from the registered retrieved images and output to the user.

28 Claims, 2 Drawing Sheets

(51) Int. Cl.
*G06T 7/33* (2017.01)
*G06T 7/00* (2017.01)

(56) References Cited

U.S. PATENT DOCUMENTS

| | | | |
|---|---|---|---|
| 2011/0200227 A1* | 8/2011 | Bogoni | G06T 7/0016 382/103 |
| 2014/0294263 A1 | 10/2014 | Hermosillo Valadez et al. | |
| 2015/0078639 A1* | 3/2015 | Hausotte | G06F 19/321 382/128 |

* cited by examiner

METHOD FOR CONTROLLING AN EVALUATION DEVICE FOR MEDICAL IMAGES OF PATIENT, EVALUATION DEVICE, COMPUTER PROGRAM AND ELECTRONICALLY READABLE STORAGE MEDIUM

PRIORITY STATEMENT

The present application hereby claims priority under 35 U.S.C. § 119 to European patent application number EP 17204143.6 filed Nov. 28, 2017, the entire contents of which are hereby incorporated herein by reference.

FIELD

Embodiments of the invention generally relate to a method for controlling an evaluation device for medical images of a patient, wherein medical images of the patient acquired at different time points are stored in an image database. Embodiments of the invention further relates to an evaluation device, a computer program and an electronically readable storage medium.

BACKGROUND

It is known in the art to store medical images of a patient, taken at different points in time, in an image database, for example in so-called PACS (Picture Archiving and Communication System). As some medical conditions develop over time, so-called "priors", medical images of the patient showing the medical condition at an earlier time point, are an important tool in assessing the current state of a medical condition, for example the progression and/or remission of a region, in particular a tumour. Thus, a common task for radiological image reading is a comparison of images acquired at multiple different time points, in some cases using different imaging modalities. The medical images may even be acquired at different institutions.

In particular, the change of lesion count and/or lesion volume (or, in general, size) is an important feature to access/stage tumours, brain lesions, liver lesions, lung lesions etc.

In current practice, a radiologist typically uses a standard viewer attached to the image database, in particular PACS, to select medical images from different time points and compare them. However, finding, assessing and documenting lesions manually across multiple time points is an error prone and time consuming process.

SUMMARY

At least one embodiment of the invention provides improved assistance to a user evaluating medical images over multiple time points, in particular without changing the image database and/or a viewer used to display the images.

Embodiments of the invention are directed to a method, an evaluation device, a computer program and an electronically readable storage medium.

In an inventive embodiment, a method is for controlling an evaluation system for medical images of a patient, wherein medical images of the patient acquired at different time points are stored in an image database, wherein, upon reception of a user command associated with a time-dependent evaluation command including at least one evaluation parameter describing an evaluation to be performed and identification information describing the patient, the method comprising:

retrieving medical images of the patient, fulfilling a relevancy criterion depending on the at least one evaluation parameter and acquired at different time points, from the image database;

registering the retrieved images, to other of the retrieved images, in at least one registration process; and deriving a composite evaluation image data set, including a time series of evaluation images, from the registered retrieved images; and outputting the composite evaluation image data set derived to the user.

At least one embodiment of the invention thus proposes an evaluation system that facilitates the reading and reporting of complex studies with existent priors, potentially from different modalities and different imaging centres/institutions. Each time a user command, for example entered in a reader for medical images and/or associated with the image database, is received, which indicates an evaluation of a time series of medical images of a certain patient regarding the time-resolved assessment of a medical condition, a composite evaluation image data set is compiled and provided dependent on the at least one evaluation parameter describing the evaluation and the identification information of the patient. The composite evaluation image data set only comprises relevant images as a time series, which are already registered to each other, facilitating the following evaluation to be performed by the user.

At least one embodiment of the invention thus proposes an evaluation device, comprising:

a memory, storing machine-executable code and storing at least one image database; and at least one processor, coupled to the memory, for executing the machine-executable code stored on the memory to configure the at least one processor to:

acquire medical images of patients, via a database interface, at different time points and storing the medical images acquired in the at least one image database;

receive a command from a user, the command being associated with a time-dependent evaluation command including at least one evaluation parameter describing an evaluation to be performed and including identification information describing a patient;

retrieve medical images of the patient from the at least one image database, the medical images fulfilling a relevancy criterion dependent on the at least one evaluation parameter and being medical images acquired at different time points;

register the medical images retrieved to other of the medical images retrieved;

derive a composite evaluation image data set including a time series of evaluation images from the retrieved medical images registered; and output to the user, the composite evaluation image data set derived.

The evaluation system realized by the method according to an embodiment of the invention can be embodied in an evaluation device, comprising a database interface to at least image database, wherein medical images of patients acquired at different time points are stored, an input unit for receiving a user command associated with a time-dependent evaluation command comprising at least one evaluation parameter describing an evaluation to be performed and identification information describing a patient, a retrieving unit for retrieving medical images of the patient fulfilling a relevancy criterion depending on the evaluation parameter and having been acquired at different time points from the image database, a registration unit for registering the retrieved images to each other, a compilation unit for deriving a composite evaluation image data set comprising a time series of evaluation images from the registered retrieved images, and an output unit for outputting the evaluation image data set to the user.

Thus, the evaluation device comprises at least one processor and is adapted to perform a method according to an embodiment of the invention. It may additionally comprise an image analysis unit for deriving feature information, as described above. All remarks regarding the method according to an embodiment of the invention also apply to the inventive evaluation device, such that the same advantages are obtained.

The evaluation system may be deployed as part of an image acquisition device, for example a magnetic resonance device, a computer tomography device or the like, or on a post-processing work station, or may be provided as a cloud service. Consequently, the evaluation device may be part of an image acquisition device, part of an post-processing work station, part of the image database, in particular a PACS, and/or realised in a cloud, providing the method as a cloud service.

A computer program according to an embodiment of the invention can be loaded into a memory of a computing device, in particular an evaluation device, and comprises program programs/segments to perform the steps of a method according to an embodiment of the invention if the computer program is executed in the computing device, in particular the evaluation device. The computer program may be stored on an electronically readable storage medium according to an embodiment of the invention, which therefore comprises stored electronically readable control information, comprising at least a computer program according to an embodiment of the invention and configured to perform the steps of a method according to an embodiment of the invention when the electronically readable storage medium is used in an evaluation device.

BRIEF DESCRIPTION OF THE DRAWINGS

Further details and advantages of the current invention can be taken from the following description of exemplary embodiments in conjunction with the drawings, in which.

DETAILED DESCRIPTION OF THE EXAMPLE EMBODIMENTS

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. The present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "exemplary" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without subdividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

Most of the aforementioned components, in particular the identification unit, can be implemented in full or in part in the form of software modules in a processor of a suitable control device or of a processing system. An implementation largely in software has the advantage that even control devices and/or processing systems already in use can be easily upgraded by a software update in order to work in the manner according to at least one embodiment of the invention.

In an inventive embodiment, a method is for controlling an evaluation system for medical images of a patient, wherein medical images of a patient acquired at different time points are stored in an image database, it is provided that, upon reception of a user command associated with a time-dependent evaluation command comprising at least one evaluation parameter describing an evaluation to be performed and identification information describing the patient, medical images of the patient fulfilling a relevancy criterion depending on the evaluation parameter and having been acquired at different time points are retrieved from the image database, the retrieved images are registered to each other in at least one registration process, and a composite evaluation image data set comprising a time series of evaluation images is derived from the registered retrieved images and output to the user.

At least one embodiment of the invention thus proposes an evaluation system that facilitates the reading and reporting of complex studies with existent priors, potentially from different modalities and different imaging centres/institutions. Each time a user command, for example entered in a reader for medical images and/or associated with the image database, is received, which indicates an evaluation of a time series of medical images of a certain patient regarding the time-resolved assessment of a medical condition, a composite evaluation image data set is compiled and provided dependent on the at least one evaluation parameter describing the evaluation and the identification information of the patient. The composite evaluation image data set only comprises relevant images as a time series, which are already registered to each other, facilitating the following evaluation to be performed by the user.

The image database may preferably be a picture archiving and communication system (PACS), containing medical images of multiple patients for retrieval by medical personal. It is important to note that neither the image database nor an image reader associated with the image database, in particular a software programs/segments like a PACS viewer, has to be changed or adapted, since at least one embodiment of the inventive method could be used independently of these systems, acting only on the information exchange between the software programs/segments and the image database. That is, the evaluation image data set provided by at least one embodiment of the inventive method can be processed like any other data set retrieved by the reader, in particular having a suitable format. At least one embodiment of the invention thus addresses the fact that is not to be expected that users will change their medical image reading procedures and workflow or modernise their standard software programs/segments for retrieving and reading medical images of a patient in the near future.

The longitudinal image collection and spatial registration provided by the evaluation image data set helps the radiologist in comparing patient results directly in the existing software programs/segments, in particular PACS viewer, using standardized tools and/or paradigms. The evaluation image data set provided by at least one embodiment of the invention thus enables users to save time and effort in manually compiling the data and reformatting the medical images, for example to normalize slice positions.

The at least one evaluation parameter also describes image data acquired and/or useful for the evaluation to be performed, for example an anatomical feature to be observed, the area of interests, and/or the time span in which the anatomical feature exists. The evaluation parameter therefore allows filtering the medical images in the image data base, retrieving only medical images relevant for the evaluation to be performed. This filtering is described by the relevancy criterion. Thus, in a first step, the method according to at least one embodiment of the invention queries the image data base for all relevant medical images of the particular patient.

It should be noted at this point that the retrieved images may be two-dimensional, three-dimensional and/or acquired by different imaging devices and/or imaging modality. Further, a medical image may comprise subimages, for example in the case of three-dimensional medical images comprising different slices as subimages.

In a preferred embodiment, the evaluation images for each time point are calculated from the registered retrieved images depending on the at least one evaluation parameter. Advantageously, image data of the retrieved registered images can thus be converted to a, in particular, common format especially suitable for the evaluation described by the evaluation parameters. The image data of the registered retrieved images is pre-processed to further facilitate the evaluation to be performed by the user. For example, relevant slices for the evaluation may be automatically chosen and/or an anatomical feature to be assessed may be emphasized. Pre-processing algorithms to perform these tasks have already been proposed for particular applications, such that these pre-processing algorithms can be provided in a library accessible by the evaluation system and appropriate pre-processing algorithms can be chosen from the library depending on the at least one evaluation parameter.

In an especially preferred embodiment, if at least one of the at least one evaluation parameter defines an area of interest of the patient and/or at least one anatomical feature of the patient, the evaluation images are each calculated to show image data of the patient in a common depiction area comprising the area of interest and/or the at least one anatomical feature. While the registration of the retrieved images already defines a common coordinate system for the image data of the registered retrieved images, it can additionally be provided that all evaluation images show the same depiction area, such that a time series of two-dimensional and/or three-dimensional evaluation images is yielded as the evaluation image data set.

Such a stack of evaluation images over time points facilitates manual evaluation by the user, since scrolling through the time points and thus the time interval covered by the time points intuitively allows direct interpretation regarding the development of the medical condition over time. It is to be noted that in a case in which a medical image has no image data in a subarea of the depiction area, this area may be blanked or otherwise marked in a derived evaluation image.

As has already been noted, two-dimensional and/or three-dimensional evaluation images may be calculated. Two-dimensional evaluation images may, for example, be slices or sectional images, while three-dimensional evaluation images can be calculated as volumes or the like.

Preferably, if the registered retrieved images comprise images acquired by different images modalities, at least one conversion algorithm is applied to image data of at least one of the imaging modalities to calculate virtual image data of at least one other of the imaging modalities. The image data used for the evaluation images may thus be converted to convey the same optical impression, regardless of the imaging modality used. There have, for example, already been proposed conversion algorithms for converting x-ray data into magnetic resonance data and vice versa. Such conversion algorithms can also be used in the scope of a current embodiment of the invention to further facilitate interpretation of the evaluation images and thus the evaluation by the user itself.

In a preferred embodiment, if at least one retrieved image comprises a plurality of two-dimensional slices and/or sectional images as subimages, at least the subimages having the highest suitability measure for the evaluation described by the evaluation parameter is included into the evaluation image data set.

For example, if the evaluation parameter describes at least one anatomical feature to be analysed, the subimage providing the best image quality of the anatomical feature and/or where the anatomical feature is depicted with the largest size, e. g. diameter, is chosen to be included into the evaluation image data set. Of course, also other suitability measures describing suitably of the corresponding subimages for the evaluation can be used, for example suitability measures taking resolution of an anatomical feature of interest and/or contrasts of the anatomical feature of interest into account. In the case of lesions, in particular tumours, it is, however, preferred to at least include the subimages showing the largest extension of the lesion into the evaluation image data set. A suitability measure therefore in general allows to include the image data best suited for the evaluation to be performed to be included into the evaluation image data set.

As already noted, a plurality of registration algorithms has been proposed for a plurality of different configurations of medical images, so that these registration algorithms can also be used when implementing an embodiment of the current invention. Preferably, multiple registration algorithm are available in a registration algorithm library, wherein at least one registration algorithm to be applied is selected depending on image data of the retrieved images and/or acquisition parameters of the retrieved images and/or image modalities of the retrieved images. In this manner, optimal registration algorithms can be chosen providing a high quality of registration of the evaluation images.

In concrete embodiments, at least one acquisition parameter describing acquisition geometry of the medical image is stored with each medical image in the image database, wherein the registration is performed using the at least one acquisition parameter of at least one retrieved image, and/or anatomical featured shown in retrieved images to be registered are identified and used for registration of the retrieved images and/or rigid and/or deformable registration if used. Standard image registration, rigid and deformable, can be used to register the retrieved images across multiple time points and potentially multiple modalities. As a result of the registration, the registered retrieved images use the same special coordinate system and can be compared over time points.

Regarding the storage of additional metadata concerning medical images, in particular acquisition parameters and/or annotation information from earlier evaluations, it is preferred that the medical images are stored in DICOM format. DICOM is a well-known format for storing and possessing medical image data, allowing to add metadata to the actual image data, i.e. the payload data. Preferably, also the evaluation image data set is determined in DICOM format, which can be used by known software programs/segments associated with the image database without any changes or required conversions.

In an especially preferred embodiment, if at least one of the at least one evaluation parameter describes at least one anatomical feature as the subject of the evaluation, an image analysis algorithm is applied to the evaluation images to derive feature information on the anatomical feature for all time points. It is thus possible to calculate quantitative comparisons between these evaluation images, such that additional value is added to the evaluation image data set. Quantitative measures may be provided in addition to the evaluation images, which can also be output, in particular displayed to the user.

Preferably, at least one annotation information stored with at least one retrieved image in the image database is used in determining the feature information and/or the image analysis algorithm comprises a segmentation regarding the at least one anatomical feature, wherein segmentation results at at least one time point are applied to segmentation at at least one other time point. The annotation information may be determined during a first evaluation of the medical image after its acquisition, for example for diagnosis and/or reporting purposes. The annotation information may be included in DICOM metadata. Such annotation information may in particular, comprise location information of anatomical features in image data of the medical image, for example a mapping to an anatomical atlas or markers for lesions and other abnormalities. If the annotation information does not describe the location of the anatomical feature anyway, it can serve as an expedient starting point for a segmentation process.

As the registered retrieved images and thus the evaluation images are registered, location information and/or segmentation information regarding an anatomical feature can be transferred between images and thus time points. In particular, it is possible to localise the anatomical feature in a first evaluation image or registered retrieved image and/or an evaluation image or registered retrieved image best suited for segmentation and then transfer the location and/or segmentation information from this evaluation image to further evaluation images or registered retrieved images, for example to initialize a segmentation process in these further images.

Preferably, at least one quantitative value describing the temporal change a property of the at least one anatomical feature is determined as the feature information. In particular, the property may comprise at least one geometrical property of the at least one anatomical feature, in particular the size of the at last one anatomical feature (diameter, volume, etc.), and/or a count of anatomical features of a type defined by at least one of the at least one evaluation parameter. Regarding lesions, in particular tumours, it is thus possible to, for example, quantify volumes and/or the number of lesions in an area of interest over time. These quantitative values can, for example, be used to calculate a growth rate and the like. In this manner, valuable additional, quantitative information may be provided to the user, adding in the evaluation.

Preferably, at least one RECIST information is derived from the time-resolved feature information. RECIST (Response Evaluation Criteria In Solid Tumours) is a set of published rules that define when tumours in cancer patients improve ("respond"), stay the same ("stabilized"), or worsen ("progress") during treatment. The determination of time-resolved feature information, in particular quantitative values, allows an automated assessment of the treatment according these rules. This adds additional useful information for the evaluation by the user.

In a preferred embodiment the feature information is output with, in particular integrated into, the evaluation image data set and/or additionally to the evaluation image data set. If the evaluation image data set is output on a display device, for example using a software programs/ segments associating with the image database, the feature information may also be displayed, preferably integrated into respective evaluation images. For example, the feature information may be overlaid onto respective evaluation images concerning at least one time point relating to the feature information. The feature information may also be used to flag important areas of the evaluation images, for example marking an anatomical feature with significant change over time. If lesions, in particular tumours, are to be evaluated, preferably growing or shrinking lesions and/or unchanged lesions may be emphasized in the evaluation images. The invention also allows to use the feature information for sorting and/or filtering the evaluation images before output. For example, evaluation images may be sorted by relevancy, displaying the evaluation images having fast-growing and/or not remitting tumours first. In this manner, the most important information for evaluation can be presented with a higher priority.

The evaluation systems realized by the method according to an embodiment of the invention can be embodied in an evaluation device, comprising
- a database interface to at least image database, wherein medical images of patients acquired at different time points are stored,
- an input unit for receiving a user command associated with a time-dependent evaluation command comprising at least one evaluation parameter describing an evaluation to be performed and identification information describing a patient,
- a retrieving unit for retrieving medical images of the patient fulfilling a relevancy criterion depending on the evaluation parameter and having been acquired at different time points from the image database,
- a registration unit for registering the retrieved images to each other,
- a compilation unit for deriving a composite evaluation image data set comprising a time series of evaluation images from the registered retrieved images, and
- an output unit for outputting the evaluation image data set to the user.

Thus, the evaluation device comprises at least one processor and is adapted to perform a method according to an embodiment of the invention. It may additionally comprise an image analysis unit for deriving feature information, as described above. All remarks regarding the method according to an embodiment of the invention also apply to the inventive evaluation device, such that the same advantages are obtained.

The evaluation system may be deployed as part of an image acquisition device, for example a magnetic resonance device, a computer tomography device or the like, or on a post-processing work station, or may be provided as a cloud service. Consequently, the evaluation device may be part of an image acquisition device, part of an post-processing work station, part of the image database, in particular a PACS, and/or realised in a cloud, providing the method as a cloud service.

A computer program according to an embodiment of the invention can be loaded into a memory of a computing device, in particular an evaluation device, and comprises program programs/segments to perform the steps of a method according to an embodiment of the invention if the computer program is executed in the computing device, in particular the evaluation device. The computer program may be stored on an electronically readable storage medium according to an embodiment of the invention, which therefore comprises stored electronically readable control information, comprising at least a computer program according to an embodiment of the invention and configured to perform the steps of a method according to an embodiment of the invention when the electronically readable storage medium is used in an evaluation device.

Figure 1:
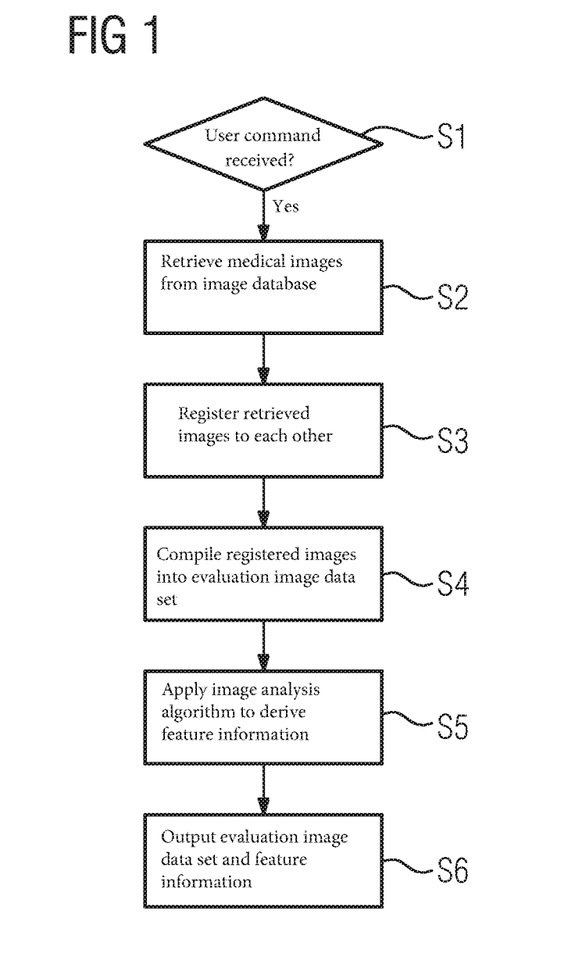
FIG. 1 is a flow chart of an embodiment of the method according to the invention.

FIG. 1 shows a flow chart of an embodiment of the method according to the invention. This embodiment functions as a modifying interface between an image database, in particular a PACS, and a software programs/segments associated with the image data base for viewing and evaluating medical images stored therein (PACS viewer/reader). The image database contains medical images of a plurality of the patient in DICOM format, which may have been acquired at different time points and/or with different modalities and/or different images acquisition devices, wherein even medical images from different institutions/imaging centres may be stored in the image database. As the medical images are stored in DICOM format, metadata is associated with them, comprising acquisition parameters and annotation information from earlier evaluation processes. The metadata also describes the image area of the patient, anatomical features visible in the medical image and image quality of the medical image, in particular for different features/properties.

According to step S1, it is monitored if a user command regarding a time-dependent evaluation to be performed is received. Such a user command comprises evaluation parameters describing the evaluation to be performed as well as an identification information describing the patient concerned.

If such a user command is received in step S1, in a step S2, medical images of the patient fulfilling a relevancy criterion using the evaluation parameter and which have been acquired at different time points are retrieved from the image data base. The evaluation system thus queries the PACS for all relevant image data of the patient identified by the identification information. If, for example, the treatment of a tumour or, in general, lesion is to be assessed in the evaluation using so-called priors, that is, medical images that were acquired at earlier points in time, only medical images showing the lesion as the anatomical feature of interest or showing lesions of the type of interest in general are retrieved. In this manner the evaluation parameter is used to find the relevant medical images in the image data base by correspondingly formulating the query.

In step S3, the retrieved images are all registered to each other, such that they use a common spatial coordinate system. Suitable registration algorithms can be chosen from a corresponding registration algorithm library, taking into account the metadata associated with the retrieved images, which can also be used during the registration process themselves. For example, annotation information can be used to locate an anatomical feature used for registration and the like. Registration algorithms for rigid and/or deformable registration can be used, depending on the concrete retrieved images.

In as step S4, the registered retrieved images are compiled into an evaluation image data set, which contains at least one time series of evaluation images, which at least in part have been calculated from the registered retrieved images. The evaluation images may be two-dimensional and/or three-dimensional, as also the medical images may be two-dimensional or three-dimensional. The evaluation images are derived from the registered retrieved images to in the best possible way facilitate the evaluation to be performed by the user when viewing these evaluation images.

In this concrete embodiment, if tumour treatment or, in general, lesion treatment is to be assisted, the depiction area is chosen in which the lesions and the anatomical features of interest are found. For example, the slice may be chosen as a depiction area wherein a corresponding lesion is best discernible and/or visible in the greatest size. Of course, multiple depiction areas relating to different time series of the evaluation image data set may be used. Sub-areas of the depiction area in which no image data at one time point is available may be correspondingly marked and/or blanked out. In summary, an evaluation image data set with at least one time series relating to a respective depiction area is yielded, such that the user can scroll to these evaluation images and intuitively assess the temporal development of the anatomical feature, i.e. the lesion.

Optionally, if at least two of the registered retrieved images have been acquired by different imaging modalities, at least one conversion algorithms can be used to convert image data of at least one of the imaging modalities to virtual image data of the other imaging modality for at least some registered retrieved images, such that the same optical impression is achieved.

The depiction area and/or the subimages/image data of the registered retrieved images to be included into the evaluation images may also be chosen dependent on a suitability measure, such that the subimage/image data having the highest suitability measure for the evaluation described by the evaluation parameter is included into the evaluation image data set. In such a manner, the best image quality of the anatomical feature, in particular the lesion, and/or the largest depiction of the anatomical feature can be included into the evaluation data set.

In step S5, an image analysis algorithm is applied to the evaluation images and/or the registered retrieved images to derive feature information on the anatomical feature for all time points. To localise the anatomical feature, i.e. the lesion, in the images, again annotation information of the metadata can be used. If the anatomical feature has yet not been segmented, a segmentation algorithm can be used to segment the anatomical feature, wherein segmentation information of one image can be used for segmentation in other images, since the images are registered to each other.

In this embodiment, regarding lesions as an anatomical feature to be evaluated, quantitative values describing geometrical properties, in particular the size, and the number on anatomical features of the type of the lesion are derived from the image data. That is, the volumes and numbers of lesion in the registered image data can be quantified. Further feature information may be derived from these quantitative values, for example growth rates and the like. In particular, RECIST information can be derived from the time-resolved quantitative values.

In a step S6, the evaluation image data set and the feature information are output to the user, in particular using the software programs/segments as described above to display the evaluation images and the feature information. The feature information may be used to modify the evaluation images or be shown overlaid onto evaluation images, for example to flag important areas of the evaluation images, in particular lesions with strong (or without) significant growth. It is noted that it is also possible to use the feature information for sorting/filtering the evaluation images before output to present the most important information first to the user.

Figure 2:
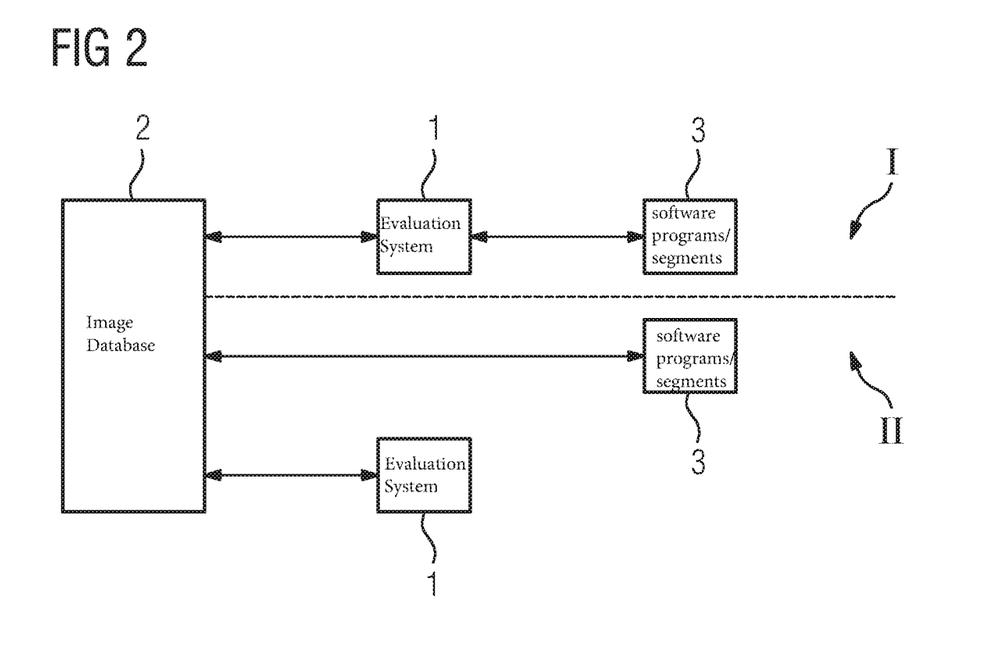
FIG. 2 shows a principle drawing of the functional location of the evaluation system.

FIG. 2 shows two possible functional realisations of the evaluation system 1. In a first embodiment the evaluation system 1 realized by the above described method is interposed between the image data base 2 and the software programs/segments 3, functioning as a modification module.

In a second embodiment, the evaluation system may be addressed only by the image database 2, when it receives a user command as described regarding step S1. The evaluation system 1 then compiles the evaluation data set and the feature information which is then sent back to the image database 2, which provides the software programs/segments 3 with the evaluation image data set and the feature information.

Figure 3:
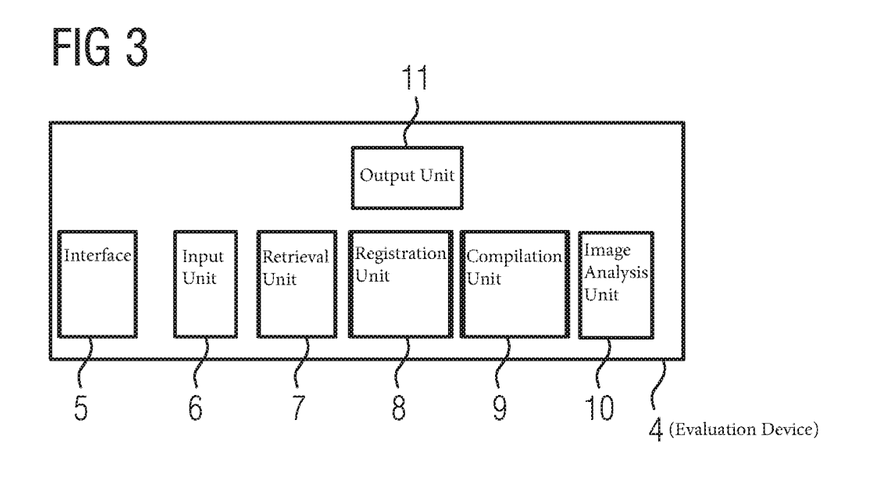
FIG. 3 shows the functional structure of an evaluation device according to an embodiment of the invention.

FIG. 3 finally shows an embodiment of the functional structure of an evaluation device for realizing the evaluation system 1. The evaluation device 4 comprises an interface 5 to the image database 2, an input unit 6 for receiving the user command, a retrieval unit 7 for retrieving the relevant medical images, a registration unit 8 for registering the retrieved images to each other, a compilation unit 9 for determining the evaluation image data set and an image analysis unit 10 for determining the feature information. An output unit 11 allows output to the software programs/segments 3 or directly to a display device.

The evaluation device 4 may be part on an image acquisition device, of a post-processing work station, of the image database 2 and/or may be realised in a cloud, providing the method as a cloud service.

Although the present invention has been described in detail with reference to the preferred embodiment, the present invention is not limited by the disclosed examples from which the skilled person is able to derive other variations without departing from the scope of the invention.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for controlling an evaluation system for medical images of a patient, the method comprising:

retrieving a plurality of medical images of the patient from an image database in response to receiving a time-dependent evaluation command, the plurality of medical images of the patient being acquired at different time points, the time-dependent evaluation command including at least one evaluation parameter and identification information of the patient, the at least one evaluation parameter corresponding to an evaluation to be performed, the at least one evaluation parameter including at least one region of interest or at least one anatomical feature, and the plurality of medical images fulfilling a relevancy criterion depending on the at least one evaluation parameter;

registering a first medical image among the plurality of medical images to one or more second medical images among the plurality of medical images to obtain a plurality of registered images;

deriving a composite evaluation image data set including a time series of evaluation images, the time series of evaluation images being a subset of the plurality of registered images selected based on,
- an image quality of the at least one region of interest or the at least one anatomical feature in each of the plurality of registered images, or
- a size of the at least one region of interest or the at least one anatomical feature in each of the plurality of registered images; and outputting the composite evaluation image data set.

2. The method of claim 1, further comprising:
calculating the time series of evaluation images based on the plurality of registered images and the at least one evaluation parameter, the time series of evaluation images corresponding to the different time points.

3. The method of claim 2, wherein the calculating calculates the time series of evaluation images such that the time series of evaluation images includes a common depiction area including the at least one region of interest or the at least one anatomical feature.

4. The method of claim 3, wherein the time series of evaluation images includes at least one of two-dimensional evaluation images or three-dimensional evaluation images.

5. The method of claim 3, further comprising:
applying at least one conversion algorithm to image data of a first imaging modality to calculate virtual image data of a second imaging modality based on at least two of the plurality of medical images, the at least two of the plurality of medical images being acquired from different imaging modalities, the different imaging modalities including the first imaging modality and the second imaging modality.

6. The method of claim 2, wherein the time series of evaluation images includes at least one of two-dimensional evaluation images or three-dimensional evaluation images.

7. The method of claim 2, further comprising:
storing at least one acquisition parameter corresponding to acquisition geometry of the plurality of medical images,
wherein the registering includes at least one of
registering the first medical image to the one or more second medical images based on the at least one acquisition parameter of at least one of the first medical image or the one or more second medical images,
registering the first medical image to the one or more second medical images based on a particular anatomical feature identified in at least one of the first medical image or the one or more second medical images, or
registering the first medical image to the one or more second medical images using at least one of rigid registration or deformable registration.

8. The method of claim 2, wherein the plurality of medical images are stored in the image database in DICOM format.

9. The method of claim 1, further comprising:
storing at least one acquisition parameter corresponding to acquisition geometry of the plurality of medical images,
wherein the registering includes at least one of
registering the first medical image to the one or more second medical images based on the at least one acquisition parameter of at least one of the first medical image or the one or more second medical images,
registering the first medical image to the one or more second medical images based on a particular anatomical feature identified in at least one of the first medical image or the one or more second medical images, or
registering the first medical image to the one or more second medical images using at least one of rigid registration or deformable registration.

10. The method of claim 1, wherein the plurality of medical images are stored in the image database in DICOM format.

11. The method of claim 1, wherein
the at least one evaluation parameter includes the at least one anatomical feature; and
the method further includes applying an image analysis algorithm to the time series of evaluation images to derive feature information on the at least one anatomical feature for the different time points.

12. The method of claim 11, wherein the applying an image analysis algorithm includes at least one of:
deriving the feature information based on annotation information stored with at least one of the plurality of medical images in the image database, or
performing a segmentation regarding the at least one anatomical feature, the performing a segmentation including applying segmentation results of a first segmentation at a first time point among the different time points to a second segmentation at a second time point among the different time points.

13. The method of claim 12, wherein the outputting outputs the feature information with the composite evaluation image data set.

14. The method of claim 11, wherein the feature information includes at least one quantitative value corresponding to a temporal change of a property of the at least one anatomical feature.

15. The method of claim 11, wherein the outputting outputs the feature information with the composite evaluation image data set.

16. The method of claim 15, wherein outputting outputs the composite evaluation image data set with the feature information integrated into the composite evaluation image data set.

17. The method of claim 11, further comprising at least one of:
sorting the time series of evaluation images based on the feature information; or
filtering the time series of evaluation images based on the feature information.

18. The method of claim 11, wherein outputting outputs the composite evaluation image data set with the feature information integrated into the composite evaluation image data set.

19. A non-transitory computer readable medium storing a computer program for execution on an evaluation device, the evaluation device being configured, upon execution of the computer program, to perform the method of claim 1.

20. A non-transitory electronically readable memory, storing a computer program for execution on an evaluation device, the evaluation device being configured, upon execution of the computer program, to perform the method of claim 1.

21. The method of claim 1, wherein the at least one evaluation parameter includes the at least one region of interest, the at least one anatomical feature and at least one time span.

22. The method of claim 1, wherein the at least one evaluation parameter includes an anatomical feature type.

23. A method for controlling an evaluation system for medical images of a patient, the method comprising:
retrieving a plurality of medical images of the patient from an image database in response to receiving a time-dependent evaluation command, the plurality of medical images of the patient being acquired at different time points, the time-dependent evaluation command including at least one evaluation parameter and identification information of the patient, the at least one evaluation parameter corresponding to an evaluation to be performed, and the plurality of medical images fulfilling a relevancy criterion depending on the at least one evaluation parameter;
registering a first medical image among the plurality of medical images to one or more second medical images among the plurality of medical images to obtain a plurality of registered images;
deriving a composite evaluation image data set including a time series of evaluation images, the time series of evaluation images including at least one of two-dimensional evaluation images or three-dimensional evaluation images;
outputting the composite evaluation image data set; and
applying at least one conversion algorithm to image data of a first imaging modality to calculate virtual image data of a second imaging modality based on at least two of the plurality of medical images, the at least two of the plurality of medical images being acquired from different imaging modalities, the different imaging modalities including the first imaging modality and the second imaging modality.

24. An evaluation device, comprising:
a database interface configured to communicate with at least one image database, a plurality of medical images of a patient acquired at different time points being stored in the at least one image database; and
processing circuitry configured to
retrieve the plurality of medical images from the at least one image database in response to a time-dependent evaluation command, the time-dependent evaluation command including at least one evaluation parameter and identification information of the patient, the at least one evaluation parameter corresponding to an evaluation to be performed, the at least one evaluation parameter including at least one region of interest or at least one anatomical feature, and the plurality of medical images fulfilling a relevancy criterion dependent on the at least one evaluation parameter,
register a first medical image among the plurality of medical images to one or more second medical images among the plurality of medical images to obtain a plurality of registered images,
derive a composite evaluation image data set including a time series of evaluation images, the time series of evaluation images being a subset of the plurality of registered images selected based on,
an image quality of the at least one region of interest or the at least one anatomical feature in each of the plurality of registered images, or
a size of the at least one region of interest or the at least one anatomical feature in each of the plurality of registered images, and output the composite evaluation image data set.

25. The evaluation device of claim 24, wherein the processing circuitry is configured to calculate the time series of evaluation images based on the plurality of registered images and the at least one evaluation parameter, the time series of evaluation images corresponding to the different time points.

26. An evaluation device, comprising:
a memory storing machine-executable code and at least one image database; and
processing circuitry coupled to the memory and configured to execute the machine-executable code to
acquire a plurality of medical images of a plurality of patients at different time points via a database interface,
store the plurality of medical images in the at least one image database,
receive a time-dependent evaluation command including at least one evaluation parameter and identification information of a patient, the at least one evaluation parameter corresponding to an evaluation to be performed, and the at least one evaluation parameter including at least one region of interest or at least one anatomical feature,
retrieve two or more medical images of the patient from the at least one image database, the two or more medical images fulfilling a relevancy criterion dependent on the at least one evaluation parameter and being acquired at different time points,
register a first medical image among the two or more medical images to one or more second medical images among the two or more medical images to obtain a plurality of registered images,
derive a composite evaluation image data set including a time series of evaluation images based on the plurality of registered images, the time series of evaluation images being a subset of the plurality of registered images selected based on,
an image quality of the at least one region of interest or the at least one anatomical feature in each of the plurality of registered images, or
a size of the at least one region of interest or the at least one anatomical feature in each of the plurality of registered images, and output the composite evaluation image data set.

27. The evaluation device of claim 26, wherein the processing circuitry is configured to calculate the time series of evaluation images based on the plurality of registered images and the at least one evaluation parameter, the time series of evaluation images corresponding to the different time points.

28. A method for controlling an evaluation system for medical images of a patient, the method comprising:
retrieving a plurality of medical images of the patient from an image database in response to receiving a time-dependent evaluation command, the plurality of medical images of the patient being acquired at different time points, the time-dependent evaluation command including at least one evaluation parameter and identification information of the patient, the at least one evaluation parameter corresponding to an evaluation to be performed, the at least one evaluation parameter including at least one region of interest or at least one anatomical feature, and the plurality of medical images fulfilling a relevancy criterion depending on the at least one evaluation parameter;

registering a first medical image among the plurality of medical images to one or more second medical images among the plurality of medical images to obtain a plurality of registered images;

deriving a composite evaluation image data set including a time series of evaluation images, the time series of evaluation images being selected from among the plurality of registered images based on a quality or a size of the at least one region of interest or the at least one anatomical feature in each of the plurality of registered images;

performing a segmentation regarding the at least one region of interest or the at least one anatomical feature, the performing a segmentation including applying segmentation results of a first segmentation at a first time point among the different time points to a second segmentation at a second time point among the different time points; and outputting the composite evaluation image data set.

* * * * *